United States Patent
Krebs et al.

(10) Patent No.: US 12,121,441 B2
(45) Date of Patent: Oct. 22, 2024

(54) BONE VOID FORMING APPARATUS

(71) Applicant: Howmedica Osteonics Corp., Mahwah, NJ (US)

(72) Inventors: Viktor Erik Krebs, Rocky River, OH (US); Lorie Continelli, Ridgewood, NJ (US); Nicole Murray, West Milford, NJ (US); Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 230 days.

(21) Appl. No.: 17/501,320

(22) Filed: Oct. 14, 2021

(65) Prior Publication Data

US 2022/0061994 A1 Mar. 3, 2022

Related U.S. Application Data

(63) Continuation of application No. 16/380,357, filed on Apr. 10, 2019, now Pat. No. 11,173,034, which is a
(Continued)

(51) Int. Cl.
*A61F 2/30* (2006.01)
*A61B 17/16* (2006.01)
(Continued)

(52) U.S. Cl.
CPC .............. *A61F 2/30* (2013.01); *A61B 17/164* (2013.01); *A61B 17/1675* (2013.01);
(Continued)

(58) Field of Classification Search
CPC .. A61F 2/30; A61F 2/36; A61F 2/3676; A61F 2/38; A61F 2/3859; A61F 2/40;
(Continued)

(56) References Cited

U.S. PATENT DOCUMENTS

| | | |
|---|---|---|
| 3,859,669 A | 1/1975 | Shersher et al. |
| 3,924,274 A | 12/1975 | Heimke et al. |

(Continued)

FOREIGN PATENT DOCUMENTS

| | | |
|---|---|---|
| DE | 2842847 A1 | 4/1980 |
| DE | 102010044571 A1 | 3/2012 |

(Continued)

OTHER PUBLICATIONS

Depuy, S-ROM Noiles Rotating Hinge, Surgical Technique and Reference Guide, 2002, 44 pages.
(Continued)

*Primary Examiner* — Christopher J Beccia
(74) *Attorney, Agent, or Firm* — Lerner David LLP

(57) ABSTRACT

A bone void forming assembly includes a support member having a head portion and an elongate portion extending therefrom. A guide member is connected to the support member and has a guide body including a channel extending therethrough. The channel defines an axis offset and obliquely angled relative to an axis of the elongate portion. The assembly also includes reamer having a cutting head and a stop member. A bushing is slidably connected to the reamer between the stop member and cutting head and is slidably connectable to the guide body via the channel.

20 Claims, 4 Drawing Sheets

Related U.S. Application Data continuation of application No. 14/992,726, filed on Jan. 11, 2016, now Pat. No. 10,299,929.

(60) Provisional application No. 62/102,260, filed on Jan. 12, 2015.

(51) Int. Cl.
| | |
|---|---|
| *A61B 17/17* | (2006.01) |
| *A61F 2/36* | (2006.01) |
| *A61F 2/38* | (2006.01) |
| *A61F 2/40* | (2006.01) |
| *A61B 90/00* | (2016.01) |
| *A61F 2/28* | (2006.01) |

(52) U.S. Cl.
CPC ...... *A61B 17/1764* (2013.01); *A61F 2/30734* (2013.01); *A61F 2/3676* (2013.01); *A61F 2/3859* (2013.01); *A61F 2/389* (2013.01); *A61F 2/4059* (2013.01); *A61B 17/1725* (2013.01); *A61B 2090/062* (2016.02); *A61F 2002/2835* (2013.01); *A61F 2002/2892* (2013.01); *A61F 2002/30738* (2013.01); *A61F 2002/30774* (2013.01); *A61F 2002/30784* (2013.01); *A61F 2002/30879* (2013.01); *A61F 2002/4077* (2013.01)

(58) Field of Classification Search
CPC ..... A61F 2/4059; A61B 17/16; A61B 17/164; A61B 17/1675
See application file for complete search history.

(56) References Cited

U.S. PATENT DOCUMENTS

| | | |
|---|---|---|
| 3,979,778 A | 9/1976 | Stroot |
| 3,986,212 A | 10/1976 | Sauer |
| 4,045,825 A | 9/1977 | Stroot |
| 4,045,826 A | 9/1977 | Stroot |
| 4,065,817 A | 1/1978 | Branemark et al. |
| 4,158,893 A | 6/1979 | Swanson |
| 4,306,550 A | 12/1981 | Forte |
| 4,341,206 A | 7/1982 | Perrett et al. |
| 4,355,427 A | 10/1982 | Schneider |
| 4,463,444 A | 7/1984 | Daniels et al. |
| 4,549,319 A | 10/1985 | Meyer |
| 4,681,589 A | 7/1987 | Tronzo |
| 4,693,721 A | 9/1987 | Ducheyne |
| 4,714,471 A | 12/1987 | Grundei |
| 4,714,475 A | 12/1987 | Grundei et al. |
| 4,728,335 A | 3/1988 | Jurgutis |
| 4,735,625 A | 4/1988 | Davidson |
| 4,738,256 A | 4/1988 | Freeman et al. |
| 4,751,922 A | 6/1988 | DiPietropolo |
| 4,777,942 A | 10/1988 | Frey et al. |
| 4,790,852 A | 12/1988 | Noiles |
| 4,822,366 A | 4/1989 | Bolesky |
| 4,846,839 A | 7/1989 | Noiles |
| 4,944,757 A | 7/1990 | Martinez et al. |
| 4,997,448 A | 3/1991 | Filer |
| 5,006,121 A | 4/1991 | Hafeli |
| 5,011,496 A | 4/1991 | Forte et al. |
| 5,035,717 A | 7/1991 | Brooks |
| 5,047,033 A | 9/1991 | Fallin |
| 5,049,157 A | 9/1991 | Mittelmeier et al. |
| 5,061,287 A | 10/1991 | Feiler |
| 5,080,685 A | 1/1992 | Bolesky et al. |
| 5,089,004 A | 2/1992 | Averill et al. |
| 5,108,398 A | 4/1992 | McQueen et al. |
| 5,122,134 A | 6/1992 | Borzone et al. |
| 5,152,797 A | 10/1992 | Luckman et al. |
| 5,169,402 A | 12/1992 | Elloy |
| 5,190,548 A | 3/1993 | Davis |
| 5,192,283 A | 3/1993 | Ling et al. |
| 5,342,363 A | 8/1994 | Richelsoph |
| 5,342,366 A | 8/1994 | Whiteside et al. |
| 5,358,526 A | 10/1994 | Tornier |
| 5,387,218 A | 2/1995 | Meswania |
| 5,403,320 A | 4/1995 | Luman et al. |
| 5,411,505 A | 5/1995 | Mumme |
| 5,441,501 A | 8/1995 | Kenyon |
| 5,445,642 A | 8/1995 | McNulty et al. |
| 5,480,453 A | 1/1996 | Burke |
| 5,489,311 A | 2/1996 | Cipolletti |
| 5,496,324 A | 3/1996 | Barnes |
| 5,507,832 A | 4/1996 | Michielli et al. |
| 5,527,316 A | 6/1996 | Stone et al. |
| 5,534,005 A | 7/1996 | Tokish, Jr. et al. |
| 5,540,694 A | 7/1996 | DeCarlo, Jr. et al. |
| 5,591,233 A | 1/1997 | Kelman et al. |
| 5,634,927 A | 6/1997 | Houston et al. |
| 5,649,299 A | 7/1997 | Battin et al. |
| 5,674,223 A | 10/1997 | Cipolletti |
| 5,702,486 A | 12/1997 | Craig et al. |
| 5,741,335 A | 4/1998 | Gerber et al. |
| 5,755,720 A | 5/1998 | Mikhail |
| 5,755,793 A | 5/1998 | Smith et al. |
| 5,766,261 A | 6/1998 | Neal et al. |
| 5,782,921 A | 7/1998 | Colleran et al. |
| 5,824,097 A | 10/1998 | Gabriel et al. |
| 5,906,644 A | 5/1999 | Powell |
| 5,931,841 A | 8/1999 | Ralph |
| 5,944,758 A | 8/1999 | Mansat et al. |
| 5,951,603 A | 9/1999 | O'Neil et al. |
| 5,957,925 A | 9/1999 | Cook et al. |
| 5,976,145 A | 11/1999 | Kennefick, III |
| 5,976,147 A | 11/1999 | LaSalle et al. |
| 5,984,968 A | 11/1999 | Park |
| 5,989,257 A | 11/1999 | Tidwell et al. |
| 5,989,261 A | 11/1999 | Walker et al. |
| 5,993,455 A | 11/1999 | Noble |
| 6,010,534 A | 1/2000 | O'Neil et al. |
| 6,045,556 A | 4/2000 | Cohen |
| 6,053,945 A | 4/2000 | O'Neil et al. |
| 6,071,311 A | 6/2000 | O'Neil et al. |
| 6,127,596 A | 10/2000 | Brown et al. |
| 6,139,584 A | 10/2000 | Ochoa et al. |
| 6,152,963 A | 11/2000 | Noiles et al. |
| 6,171,342 B1 | 1/2001 | O'Neil et al. |
| 6,197,065 B1 | 3/2001 | Martin et al. |
| 6,214,052 B1 | 4/2001 | Burkinshaw |
| 6,214,053 B1 | 4/2001 | Ling et al. |
| 6,228,120 B1 | 5/2001 | Leonard et al. |
| 6,241,722 B1 | 6/2001 | Dobak et al. |
| 6,245,113 B1 | 6/2001 | Revie et al. |
| 6,264,699 B1 | 7/2001 | Noiles et al. |
| 6,283,999 B1 | 9/2001 | Rockwood, Jr. |
| 6,398,812 B1 | 6/2002 | Masini |
| 6,406,496 B1 | 6/2002 | Ruter |
| 6,440,171 B1 | 8/2002 | Doubler et al. |
| 6,494,913 B1 * | 12/2002 | Huebner ............ A61B 17/1778 606/87 |
| 6,508,841 B2 | 1/2003 | Martin et al. |
| 6,520,994 B2 | 2/2003 | Nogarin |
| 6,558,425 B2 | 5/2003 | Rockwood, Jr. |
| 6,592,622 B1 | 7/2003 | Ferguson |
| 6,702,822 B1 | 3/2004 | Noiles et al. |
| 6,712,855 B2 | 3/2004 | Martin et al. |
| 6,887,276 B2 | 5/2005 | Gerbec et al. |
| 6,902,583 B2 | 6/2005 | Gerbec et al. |
| 6,905,513 B1 | 6/2005 | Metzger |
| 6,945,556 B2 | 9/2005 | Maertens |
| 7,001,429 B2 | 2/2006 | Ferguson |
| 7,070,622 B1 | 7/2006 | Brown et al. |
| 7,074,224 B2 | 7/2006 | Daniels et al. |
| 7,090,677 B2 | 8/2006 | Fallin et al. |
| 7,108,719 B2 | 9/2006 | Horber |
| 7,112,203 B2 | 9/2006 | Le Beguec et al. |
| 7,141,073 B2 | 11/2006 | May et al. |
| 7,175,664 B1 | 2/2007 | Lakin |
| 7,255,702 B2 | 8/2007 | Serra et al. |
| 7,291,174 B2 | 11/2007 | German et al. |
| 7,297,163 B2 | 11/2007 | Huebner |

(56) References Cited

U.S. PATENT DOCUMENTS

| | | |
|---|---|---|
| 7,338,528 B2 | 3/2008 | Stone et al. |
| 7,393,355 B2 | 7/2008 | Tulkis et al. |
| 7,462,197 B2 | 12/2008 | Tornier et al. |
| 7,476,254 B2 | 1/2009 | White et al. |
| 7,481,814 B1 | 1/2009 | Metzger |
| 7,481,841 B2 | 1/2009 | Hazebrouck et al. |
| 7,507,256 B2 | 3/2009 | Heck et al. |
| 7,537,664 B2 | 5/2009 | O'Neill et al. |
| 7,556,652 B2 | 7/2009 | Angibaud et al. |
| 7,615,080 B2 | 11/2009 | Ondrla |
| 7,632,273 B2 | 12/2009 | Schnieders et al. |
| 7,670,383 B1 | 3/2010 | Brown et al. |
| 7,722,678 B2 | 5/2010 | Brown et al. |
| 7,785,328 B2 | 8/2010 | Christie et al. |
| 7,799,085 B2 | 9/2010 | Goodfried et al. |
| 7,806,936 B2 | 10/2010 | Wright |
| 7,832,405 B1 | 11/2010 | Schlueter et al. |
| 7,833,228 B1 | 11/2010 | Hershberger |
| 7,892,288 B2 | 2/2011 | Blaylock et al. |
| 7,892,290 B2 | 2/2011 | Bergin et al. |
| 7,918,892 B2 | 4/2011 | Huebner |
| 7,942,879 B2 | 5/2011 | Christie et al. |
| 7,976,545 B2 | 7/2011 | Hershberger et al. |
| 8,029,573 B2 | 10/2011 | Podolsky |
| 8,048,166 B2 | 11/2011 | Brown et al. |
| 8,052,687 B2 | 11/2011 | Sackett et al. |
| 8,105,385 B2 | 1/2012 | Maroney et al. |
| 8,118,868 B2 | 2/2012 | May et al. |
| 8,147,498 B2 | 4/2012 | Schlueter et al. |
| 8,147,861 B2 | 4/2012 | Jones et al. |
| 8,157,869 B2 | 4/2012 | Metzger et al. |
| 8,167,882 B2 | 5/2012 | Sackett et al. |
| 8,177,788 B2 | 5/2012 | McLean et al. |
| 8,177,849 B2 | 5/2012 | Meyers et al. |
| 8,182,542 B2 | 5/2012 | Ferko |
| 8,187,336 B2 | 5/2012 | Jamali |
| 8,192,497 B2 | 6/2012 | Ondrla |
| 8,226,725 B2 | 7/2012 | Ferko |
| 8,273,091 B2 | 9/2012 | Elghazaly |
| 8,337,498 B2 | 12/2012 | Rasmussen |
| 8,350,186 B2 | 1/2013 | Jones et al. |
| 8,372,157 B2 | 2/2013 | Petersen et al. |
| 8,382,849 B2 | 2/2013 | Thomas |
| 8,424,183 B2 | 4/2013 | Thomas |
| 8,444,699 B2 | 5/2013 | Metzger et al. |
| 8,460,393 B2 | 6/2013 | Smith et al. |
| 8,506,645 B2 | 8/2013 | Blaylock et al. |
| 8,535,385 B2 | 9/2013 | Hanssen et al. |
| 8,585,770 B2 | 11/2013 | Meridew et al. |
| 8,636,800 B2 | 1/2014 | Ferko et al. |
| 8,696,757 B2 | 4/2014 | Brown et al. |
| 8,715,356 B2 | 5/2014 | Porter et al. |
| 8,728,387 B2 | 5/2014 | Jones et al. |
| 8,790,402 B2 | 7/2014 | Monaghan et al. |
| 8,828,014 B2 | 9/2014 | Gross |
| 8,900,317 B2 | 12/2014 | Zubok et al. |
| 9,011,444 B2 | 4/2015 | Primiano et al. |
| 9,149,282 B2 | 10/2015 | Servidio et al. |
| 9,204,884 B2 | 12/2015 | Dees et al. |
| 9,259,257 B2 | 2/2016 | Bagga et al. |
| 9,320,527 B2 | 4/2016 | Kehres et al. |
| 9,345,523 B2 | 5/2016 | Segina et al. |
| 9,526,513 B2 | 12/2016 | Collazo et al. |
| 9,668,758 B2 | 6/2017 | Collazo et al. |
| 9,795,392 B2 | 10/2017 | Zajac |
| RE47,149 E | 12/2018 | Primiano et al. |
| 10,149,763 B2 | 12/2018 | Krebs et al. |
| 10,265,083 B2 | 4/2019 | Servidio et al. |
| 10,299,929 B2 * | 5/2019 | Collazo ............... A61F 2/30 |
| 10,335,171 B2 | 7/2019 | Collazo et al. |
| 10,524,806 B2 | 1/2020 | Collazo et al. |
| RE48,163 E | 8/2020 | Primiano et al. |
| 11,172,941 B2 | 11/2021 | Collazo et al. |
| 11,173,034 B2 | 11/2021 | Collazo |
| 2001/0009974 A1 | 7/2001 | Reisfeld |
| 2002/0016634 A1 | 2/2002 | Maroney et al. |
| 2003/0171756 A1 | 9/2003 | Fallin et al. |
| 2003/0171815 A1 | 9/2003 | Kana et al. |
| 2003/0187449 A1 | 10/2003 | McCleary et al. |
| 2004/0049285 A1 | 3/2004 | Haas |
| 2004/0092951 A1 | 5/2004 | Serra et al. |
| 2004/0162619 A1 | 8/2004 | Blaylock et al. |
| 2004/0267267 A1 | 12/2004 | Daniels et al. |
| 2005/0090902 A1 | 4/2005 | Masini |
| 2005/0177241 A1 | 8/2005 | Angibaud et al. |
| 2005/0288676 A1 | 12/2005 | Schnieders et al. |
| 2006/0041317 A1 | 2/2006 | Hazebrouck et al. |
| 2006/0147332 A1 | 7/2006 | Jones et al. |
| 2006/0241776 A1 | 10/2006 | Brown et al. |
| 2007/0088443 A1 | 4/2007 | Hanssen et al. |
| 2007/0118229 A1 | 5/2007 | Bergin et al. |
| 2007/0142914 A1 | 6/2007 | Jones et al. |
| 2007/0162033 A1 | 7/2007 | Daniels et al. |
| 2007/0225821 A1 | 9/2007 | Reubelt et al. |
| 2008/0051908 A1 | 2/2008 | Angibaud et al. |
| 2008/0147071 A1 | 6/2008 | Serra et al. |
| 2008/0161812 A1 | 7/2008 | Sackett et al. |
| 2008/0281428 A1 | 11/2008 | Meyers et al. |
| 2008/0306600 A1 | 12/2008 | Huebner |
| 2009/0157190 A1 | 6/2009 | Collazo et al. |
| 2010/0057212 A1 | 3/2010 | Thomas |
| 2010/0076565 A1 | 3/2010 | Thomas |
| 2010/0082031 A1 | 4/2010 | Sackett et al. |
| 2010/0114323 A1 | 5/2010 | Deruntz et al. |
| 2010/0222891 A1 | 9/2010 | Goodfried et al. |
| 2010/0262146 A1 | 10/2010 | Tulkis |
| 2010/0286696 A1 | 11/2010 | Christie et al. |
| 2011/0009973 A1 | 1/2011 | Meyers et al. |
| 2011/0009974 A1 | 1/2011 | Blaylock et al. |
| 2011/0015634 A1 | 1/2011 | Smith et al. |
| 2011/0130840 A1 | 6/2011 | Oskouei |
| 2011/0190899 A1 | 8/2011 | Pierce et al. |
| 2011/0213467 A1 | 9/2011 | Lozier et al. |
| 2011/0218636 A1 * | 9/2011 | Smith ............... A61B 17/1753 623/20.35 |
| 2012/0016482 A1 | 1/2012 | Mooradian et al. |
| 2012/0035733 A1 | 2/2012 | Porter et al. |
| 2012/0089146 A1 | 4/2012 | Ferko et al. |
| 2012/0209270 A1 | 8/2012 | Segina et al. |
| 2012/0226281 A1 | 9/2012 | Sackett et al. |
| 2012/0310361 A1 | 12/2012 | Zubok et al. |
| 2013/0053976 A1 | 2/2013 | Gugler et al. |
| 2013/0150858 A1 | 6/2013 | Primiano et al. |
| 2013/0172892 A1 | 7/2013 | Servidio et al. |
| 2013/0211536 A1 | 8/2013 | Metzger et al. |
| 2013/0264749 A1 | 10/2013 | Jones et al. |
| 2013/0268085 A1 | 10/2013 | Dong et al. |
| 2014/0276882 A1 | 9/2014 | Collazo et al. |
| 2014/0277528 A1 | 9/2014 | Mines et al. |
| 2014/0277567 A1 | 9/2014 | Collazo et al. |
| 2015/0105779 A1 | 4/2015 | Smith et al. |
| 2015/0190150 A1 | 7/2015 | Primiano et al. |
| 2015/0282935 A1 | 10/2015 | Kuldjanov et al. |
| 2015/0366567 A1 | 12/2015 | Servidio et al. |
| 2023/0233328 A1 | 7/2023 | Cullum et al. |

FOREIGN PATENT DOCUMENTS

| | | |
|---|---|---|
| EP | 0016480 A1 | 10/1980 |
| EP | 1570812 A1 | 9/2005 |
| EP | 2168506 A1 | 3/2010 |
| EP | 2168586 A1 | 3/2010 |
| EP | 2181672 A1 | 5/2010 |
| GB | 2159416 A | 12/1985 |
| WO | 03094698 A2 | 11/2003 |
| WO | 2006127486 A2 | 11/2006 |
| WO | 2008069800 A1 | 6/2008 |
| WO | 2009094698 A1 | 8/2009 |

OTHER PUBLICATIONS

Extended European Search Report for Application No. EP14159399 dated Jun. 6, 2014.

(56) References Cited

OTHER PUBLICATIONS

Extended European Search Report with Written Opinion for Application No. 20173076 completed Aug. 12, 2020, 6 pages.
International Search Report and Written Opinion for Application No. PCT/US2012/068473 dated Mar. 8, 2013.
International Search Report and Written Opinion for Application No. PCT/US2012/072087 dated May 2, 2013.
Jones et al., U.S. Appl. No. 13/441,154, filed Apr. 6, 2012, titled "Surface Modified Unit Cell Lattice Structures for Optimized Secure Freeform Fabrication".
Knee Revision Product Portfolio, DePuy International Ltd., a Johnson & Johnson Company, Cat. No. 9075-40-000 version 1, Copyright 2009.
Lonner, et al., Impaction Grafting and Wire Mesh for Uncontained Defects in Revision Knee Arthroplasty, Clinical Orthopaedics and Related Research, No. 404, pp. 145-151, Copyright Nov. 2002, Lippincott Williams & Wilkins, Inc.
McQueen, Wichita Fusion Nail Surgical Technique, Oct. 2006, 12 pages, Stryker.
Partial International Search Report dated Mar. 15, 2013 for Application No. PCT/US2012/072087.
Schreurs, et al., Femoral Component Revision with Use of Impaction Bone-Grafting and a Cemented Polished Stem. Surgical Technique, The Journal of Bone & Joint Surgery, Sep. 2006, pp. 259-274.
Stryker Howmedica Osteonics, X-change Revision Instruments System, Copyright Howmedica Osteonics, Sep. 2001.
Zimmer, Trabecular Metal, Tibial and Femoral Cones Surgical Techniques, Copyright 2011.

\* cited by examiner

BONE VOID FORMING APPARATUS

CROSS-REFERENCE TO RELATED APPLICATIONS

The present application is a continuation of U.S. application Ser. No. 16/380,357, filed Apr. 10, 2019, which is a continuation of U.S. application Ser. No. 14/992,726, filed Jan. 11, 2016, now U.S. Pat. No. 10,299,929, which claims the benefit of the filing date of U.S. Provisional Patent Application No. 62/102,260 filed Jan. 12, 2015, the disclosures of which are hereby incorporated herein by reference.

BACKGROUND OF THE INVENTION

Joint replacement surgery is a common orthopedic procedure to repair and replace a damaged, diseased, or otherwise unhealthy joint. These procedures generally fall into two categories: primary and revision. In a primary joint replacement, the operator replaces the native joint with prosthetic components typically by first resecting the native bone and/or cartilage and then affixing the prosthetic components to the resected bone.

A revision procedure is performed to replace the primary prosthesis, or in some instances, a previously implanted revision prosthesis. Typically, during a revision procedure, the previously implanted prosthesis is extracted and the underlying bone resurfaced in preparation for receipt of the revision prosthesis. Bone defects in the form of bone loss or deterioration are frequently exposed upon extraction of the previously implanted prosthesis. These defects often reside within the epiphyseal and metaphyseal regions of the bone and extend radially outwardly from the center of the bone. Such defects may be caused by, inter alia, osteolysis, necrosis, infection, and bone incidentally removed along with the previously implanted prosthesis. In order to account for such defects, numerous void filling implants, such as that disclosed in Noiles U.S. Pat. No. 4,846,839, for example, have been developed to fill the voids formed by these defects and to provide structural support for the bone and prosthesis.

Despite the benefits of these void filling implants, their use in complex revision procedures may further complicate the procedure. Prior to extraction of a previously implanted prosthesis, the joint must be exposed. In an example of a total knee replacement, exposure can be made difficult for a number of reasons, such as an exceptionally tight extensor mechanism, which may be due to an improperly fitted prosthesis. One technique for exposing difficult-to-expose knees is a tibial tubercle osteotomy in which the patella tendon is released from the tibia by resecting the bone surrounding the tibial tubercle, which is later resecured to the tibia by at least one fixation device, such as a bone screw or cerclage wire, for example. However, the presence of a void filler, or even an intramedullary stem, creates an obstacle for the fixation device that must be navigated, oftentimes blind, resulting in increased complication of the procedure.

In another example, a patient may suffer an extensor mechanism complication, such as patellar tendon rupture, that must be repaired during the revision procedure. The ruptured tendon may be repaired by an allograft technique where a bone plug with an attached tendon is secured to the tibia also by a fixation device. Again the presence of a void filler or intramedullary stem may interfere with such a repair.

Therefore there is a need for a void filling prosthesis that facilitates bone-to-bone fixation and tissue-to-bone fixation.

BRIEF SUMMARY OF THE INVENTION

Generally, disclosed herein are devices and methods for filling bone voids and also providing means for soft tissue and/or bone-to-bone fixation.

In one aspect of the disclosure, a void filling prosthesis, includes first and second ends defining a length therebetween and outer and inner surfaces defining a sidewall therebetween. The sidewall is at least partially curved about an axis that extends along the length. The void filling prosthesis also includes a fixation prominence extending from the outer surface and includes a first aperture extending in a direction toward the sidewall.

Additionally, the first aperture may be threaded to receive a threaded fastener. A second aperture may define a passageway extending entirely through the fixation prominence. Furthermore, a third aperture may be disposed adjacent to the first aperture. The second aperture may extend through the fixation prominence between the first and third apertures. Also, the first and third apertures may extend parallel to each other and the second aperture may extend substantially perpendicular to the first and third apertures.

Continuing with this aspect, the inner surface may include a solid material and the outer surface may include a porous material. The fixation prominence may be at least partially comprised of a porous metal material. Also, the void filler may include first and second portions and a channel extending therethrough. The channel may define the inner surface. Further, the first and second portions may each be substantially frustoconical. The void filler may also include at least one notch in the sidewall. The first portion may be configured to fit in a void formed in a metaphysis of a long bone and the second portion may be configured to fit in a void formed in a diaphysis of a long bone. The long bone may be a tibia. The fit of the first portion in the void may be a press-fit.

In another aspect of the disclosure, a void filling prosthesis includes first and second ends and an inner surface disposed therebetween. The inner surface defines a channel that extends through the entirety of the prosthesis and is configured to receive an elongate portion of a joint prosthesis therein. The void filling prosthesis also includes a fixation prominence extending from an outer surface of the prosthesis and has at least one fixation aperture.

Additionally, the at least one fixation aperture may a threaded opening. Also, the channel may extend along a longitudinal axis of the void filling prosthesis and the at least one fixation aperture may extend through the fixation prominence in a direction transverse to the longitudinal axis.

Continuing with this aspect, the at least one fixation aperture may be a plurality of fixation apertures that include a first set of fixation apertures that each have a threaded inner surface and a second set of fixation apertures that are oriented in a direction transverse to the first set of fixation apertures. The first set of fixation apertures may extend partially into the fixation prominence and the second set of fixation apertures extend through the fixation prominence.

In a further aspect of the disclosure, a prosthetic system for implantation into an end of bone includes a first prosthesis having a stem, and a second prosthesis having first and second ends and inner and outer surfaces extending between the first and second ends. The inner surface defines a channel for receipt of the stem. The outer surface has at least one fixation aperture extending therein.

Additionally, the channel may be configured to receive the stem such that a gap sufficiently large to support a cement mantle is formed between the stem and the inner surface of the second prosthesis. The second prosthesis may include a first portion configured to be received within a metaphysis of the bone and a second portion configured to be received within a diaphysis of the bone.

Continuing with this aspect, the second prosthesis may include a fixation prominence extending radially outwardly therefrom. The at least one fixation aperture may extend into the fixation prominence. The fixation prominence may extend along the first and second portions. The fixation prominence may include an intermediate segment that is at least partially cylindrical and the at least one fixation aperture may extend into the intermediate segment. The at least one fixation aperture may be threaded. The fixation prominence may include first and second flanking segments that flank the intermediate segment. The thickness of the void filler is may be greater at the intermediate segment than at the flanking segments.

In a still further aspect of the disclosure, a method of implanting a void filling prosthesis into an end of bone includes inserting a void filling prosthesis into a void in the bone. The void filling prosthesis has first and second ends and a fixation prominence extending therefrom. The fixation prominence has at least one fixation aperture. The method also includes advancing a first fixation device through the bone and at least partially into the fixation aperture.

Additionally, the inserting step may include inserting the void filling prosthesis so that the second end is disposed within the bone and the first end is flush with the end of the bone or disposed within the bone. The fixation aperture and fixation device may be correspondingly threaded. The method may also include reaming a first portion of the bone to receive a first frustoconical portion of the void filling prosthesis, and reaming a second portion of the bone to receive the fixation prominence. The method may also include inserting a body of an aiming device into the first end of the void filling prosthesis. The aiming device may include an aiming arm that has at least one guide aperture. The method may also include aligning the at least one guide aperture with at least one fixation aperture.

In yet a further aspect of the disclosure, a method of implanting a void filling prosthesis into an end of bone includes inserting a void filling prosthesis into a void in the bone. The void filling prosthesis has first and second ends and inner and outer surfaces disposed therebetween. The inner surface defines a channel that extends through the entirety of the prosthesis and is configured to receive an elongate portion of a joint prosthesis. The outer surface includes at least one fixation aperture. The method also includes advancing a first fixation device through the bone and at least partially into the fixation aperture.

Additionally, the method may also include inserting the elongate portion of a joint prosthesis into and through the channel such that at least a portion of the elongate portion extends from the second end of the void filling prosthesis.

BRIEF DESCRIPTION OF THE DRAWINGS

These and other features, aspects, and advantages of the present invention will become better understood with regard to the following description, appended claims, and accompanying drawings where:

DETAILED DESCRIPTION

When referring to specific directions in the following discussion of certain implantable devices, it should be understood that such directions are described with regard to the implantable device's orientation and position during exemplary application to the human body. Thus, as used herein, the term "proximal" means close to the heart and the term "distal" means more distant from the heart. The term "anterior" means toward the front of the body or the face and the term "posterior" means toward the back of the body. The term "medial" means toward the midline of the body and the term "lateral" means away from the midline of the body. Also, as used herein, the terms "about," "generally" and "substantially" are intended to mean that deviations from absolute are included within the scope of the term so modified.

Figure 1:
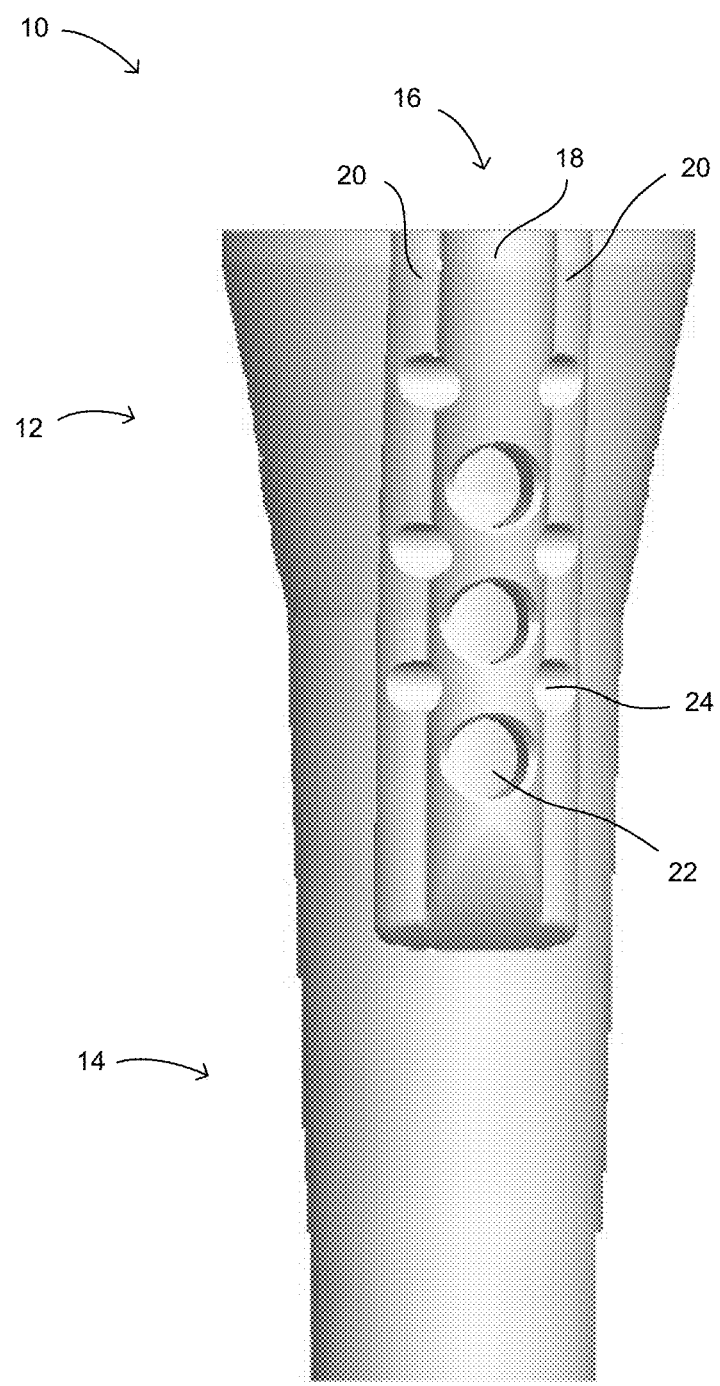
FIG. 1 is a front view of one embodiment of a void filling prosthesis.
Figure 2:
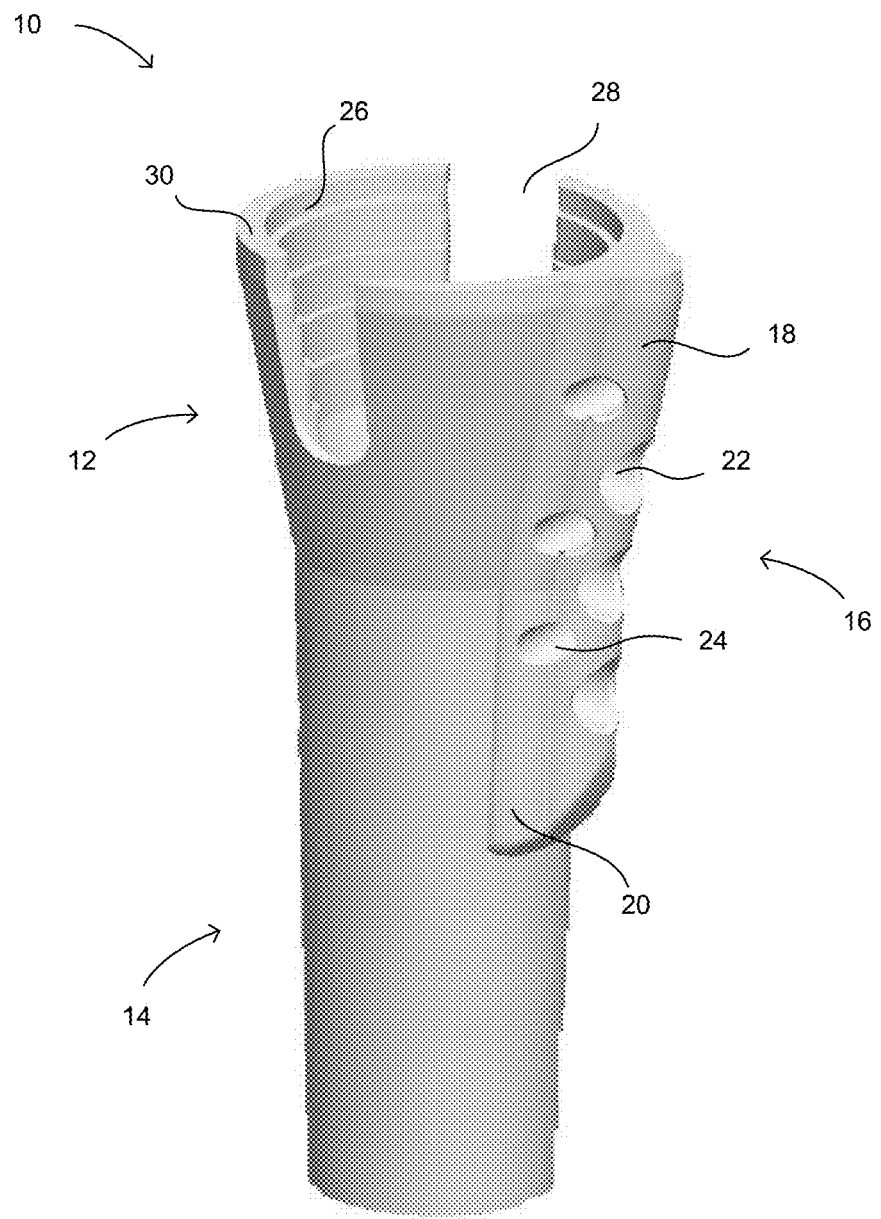
FIG. 2 is a perspective view of the void filling prosthesis of FIG. 1.

FIGS. 1 and 2 depict a void filler 10 or void filling prosthesis that is configured for placement within a void in a tibia and generally includes a metaphyseal portion or first portion 12, a diaphyseal portion or second portion 14, and a fixation prominence 16 that extends along portions of metaphyseal and diaphyseal portions 12 and 14. It is noted that, while the following discussion refers to void filler 10 in relation to a tibia, the same principles apply for a void filler that may be utilized in a proximal humerus or distal or proximal femur. Of course, it is also envisioned that the present invention may have applicability elsewhere in the body.

Metaphyseal portion 12, as shown, is generally frustoconical. However, in some embodiments, metaphyseal portion 12 may be cylindrical. In other embodiments metaphyseal portion 12 may include lobed portions, asymmetrical geometries or other geometries that extend beyond the general frustoconical shape in order to help address asymmetric or lateral and/or medial defects in the bone. Examples of alternate geometrical shapes that can be employed are disclosed in U.S. Publication Nos. 2013/0150858; 2013/0172892; 2014/0276882; and 2014/0277567, the disclosures of which are hereby incorporated-by-reference herein in their entireties.

A channel extends through metaphyseal portion 10 and defines an inner surface 26 and a sidewall 30. Inner surface 26 is preferably a stepped surface or otherwise textured surface to promote bone cement adhesion. Metaphyseal portion 12 also includes notches 28 in sidewall 30 that form a clearance space for a baseplate keel of a tibial component.

Diaphyseal portion 14 is generally cylindrical or frustoconical to substantially match the intramedullary canal of a long bone. In some embodiments, diaphyseal portion 14 may be frustoconical with a cylindrical distal end. Diaphyseal portion 14 extends distally from metaphyseal portion 12, and the channel that extends through metaphyseal portion 12 also extends through diaphyseal portion 14 so that the channel extends through the length of the entirety of void filler 10. The inner surface of diaphyseal portion 14 that is defined by this channel may also be stepped or textured to facilitate cement adhesion. The channel is preferably sized to receive a prosthesis stem and allow for sufficient space to receive and support a cement mantle such as a cement mantle that includes polymethyl methacrylate.

Fixation prominence 16 extends radially outwardly from the outer surface of diaphyseal and metaphyseal portions 12 and 14 and extends along these portions in a general proximal-distal direction. Fixation prominence 16 is preferably located in an area of void filler 10 that would be placed in an anterior or posterior position inside a tibial bone. However, fixation prominence 16 can be located in other locations, such as medial or lateral positions on void filler 10. In some embodiments, fixation prominence 16 may only extend along the metaphyseal portion 12 or diaphyseal portion 14. In other embodiments, there may be multiple fixation prominences 16 extending along void filler 10 in various locations. For example, a fixation prominence 16 may extend along void filler 10 in an anterior, posterior, lateral, and medial position.

Fixation prominence 16 generally includes an intermediate elongate segment 18 and flanking elongate segments 20 (best shown in FIG. 1). Intermediate segment 18 protrudes from the outer surface of void filler 10 further than at flanking segments 20 such that the thickness of void filler 10 at intermediate segment 18 is thicker than at flanking segments 20. This helps maximize the depth of threaded openings 22 extending into intermediate segment 18, while minimizing the amount of space taken up by void filler 10 in the bone.

Intermediate and flanking segments 18 and 20 are generally curved to form cylindrical geometries, which may be complementary to a reaming tool. However, in some embodiments flanking segments 20 may blend into intermediate segment 18 to give the appearance of a single segment. In other, embodiments, segments 18 and 20 may have other geometries, such as square or triangular geometries. At the distal end of fixation prominence 16, intermediate and flanking segments 18 and 20 are tapered to facilitate impaction into an end of bone.

Fixation prominence 16 includes fixation apertures that may be utilized to affix bone to bone and tissue to bone via various fixation means, such as threaded fasteners, cerclage wires, and sutures, for example. One such fixation aperture is a threaded opening 22 located in intermediate segment 18. Intermediate segment 18 includes a plurality of these threaded openings, which extend in a direction transverse to a longitudinal axis of void filler 10 and toward the sidewall/channel of void filler 10. The depth of threaded openings 22 is such that a threaded fastener, such as a bone screw, can be inserted through a segment of bone and into the threaded portion to create solid fixation.

Another fixation aperture is a passageway 24 that extends through fixation prominence 16 in a direction transverse to threaded openings 22. In some embodiments, the transverse direction may be substantially perpendicular with the extent of threaded openings 22. These passageways may be smooth in order to safely house a fixation wire, suture, or other flexible fixation device. Passageways 24 are generally situated or positioned through fixation prominence 16 at locations that are between each of the plurality of threaded openings so that threaded openings 22 and passageways 24 do not intersect.

While fixation prominence 16 is described and depicted as generally elongate and extending along and between diaphyseal and metaphyseal portions 12 and 14, fixation prominence 16 may be another configuration, including, but not limited to, a plurality of bumps extending outwardly from the sidewall of void filler 10 at various locations about void filler 10. Each of these bumps may be square or circular and may each include threaded opening 22 and/or passageway 24 as described above.

Also, it is contemplated that void filler 10 may not include a fixation prominence, but rather threaded openings 22 extending into sidewall 30. In such an embodiment, sidewall 30 may be thicker in order to accommodate a threaded fastener.

In some embodiments, void filler 10 may be implanted into the bone such that fixation prominence 16 faces posteriorly. In such an embodiment, void filler 10 may include circumferential grooves (not shown) within metaphyseal and diaphyseal portions 12 and 14 that allow for a wire or suture to be retained therein, when the wire is wrapped around a portion of void filler 10 from a posterior to anterior direction.

Void filler 10 can be made from any biocompatible material including stainless steel, titanium, cobalt-chromium, tantalum, niobium, or polymeric material such as PEEK. In addition, the void filler's bone contacting surfaces may be made from a porous metal such as titanium foam, and the void filler's non-bone contacting surfaces, such as inner surface 26, may be made from solid or nonporous metal. The porosity of the bone contacting surfaces allows for bony ingrowth therein. In some embodiments, the entire thickness of void filler 10 may be porous, while in other embodiments, the entire thickness of void filler 10 may be solid.

With particular regard to the construction of fixation prominence 16, fixation prominence 16 may be entirely porous while the interior of threaded apertures 22 and passageways 24 may be coated with a solid material. In some embodiments, threaded openings 22 may be lined with a material softer than that of a threaded fastener, which deforms to conform to the threaded fastener upon insertion therein. In other embodiments, fixation prominence 16 may be primarily solid while the outer surface is treated to provide the requisite porosity. As an example, such treatment may be performed by high energy beam processing, such as Selective Laser Melting ("SLM") and Electron Beam Melting ("EBM"), or other additive manufacturing processes. Examples of high energy beam processing are disclosed in U.S. Pat. Nos. 7,537,664 and 8,728,387 and U.S. Publication Nos. 2006/0147332 and 2013/0268085, the disclosures of which are hereby incorporated-by-reference herein in their entireties.

Figure 3:
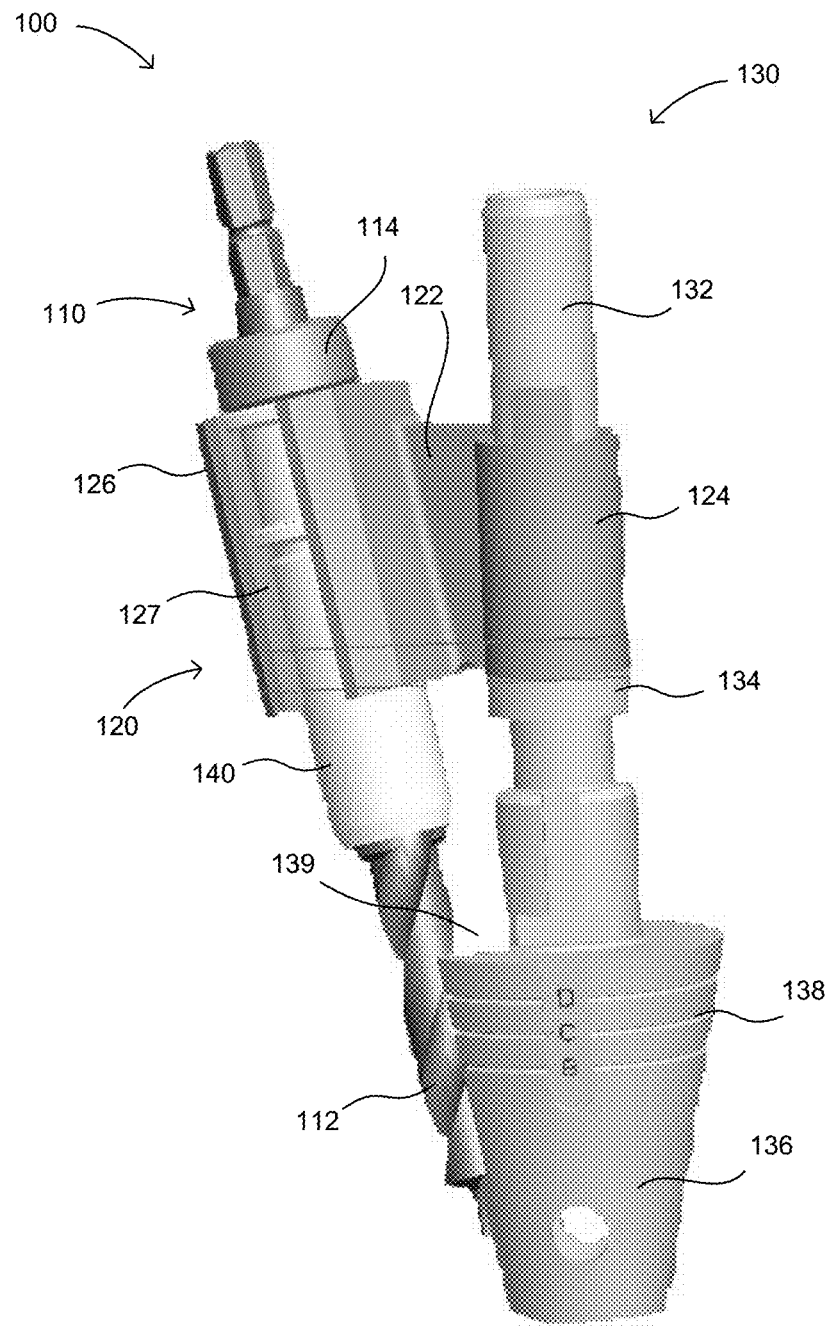
FIG. 3 is perspective view of one embodiment of a bone resection assembly.

FIG. 3 depicts a reamer assembly 100 for preparing a bone to receive void filler 10, which includes a trial 130, a reamer guide 120, a bushing 140, and a reamer 110. When implanting void filler 10, it is preferable to have the bone prepared to create a press-fit between void filler 10 and the bone such that compression of the bone promotes bony ingrowth into void filler 10. Such bone preparation can be reproducibly performed by reamer assembly 100.

Trial 130 includes a head 136 and a shaft 132. Head 136 is frustoconical to match the profile or shape of metaphyseal portion 12. Head 136 includes indicia 138, such as laser lines, to indicate the depth of head 136 in the bone. Head 136 also includes a groove 139 extending along its length to create space for cutting head 112 during the reaming process.

Reamer 110 includes a cutting head 112, a bushing 140, and a depth stop 114. Cutting head 112 is slidable within and guided by bushing 140. Depth stop 114 is located proximal to bushing 140 and during use contacts bushing 140 to indicate that cutting head 112 has reached the appropriate depth.

Reamer guide 120 includes a retaining sleeve 124 that is configured to slide over shaft 132 of trial 130. Reamer guide 120 also includes a guide collar 126 attached to retaining sleeve 124 by a flange 122 such that guide collar 126 has a longitudinal axis that is angled with respect to a longitudinal axis of retaining sleeve 124.

Guide collar 126 generally includes a slot 127 extending through a sidewall in guide collar 126. Slot 127 is in communication with a retaining channel that extends through guide collar 126. The retaining channel is sized to slidingly receive and retain bushing 140, and slot 127 is sized to allow reamer head 112, but not bushing 140, to be passed therethrough.

Reamer 100 is mounted to guide collar 126 by holding bushing 140 against depth stop 114 and passing cutting head 112 though slot 127 and into the retaining channel. Once cutting head 112 is in the retaining channel, bushing 140 is slid into the retaining channel where it is retained during the reaming process in which cutting head 112 is guided by bushing 140 into bone.

Figure 4:
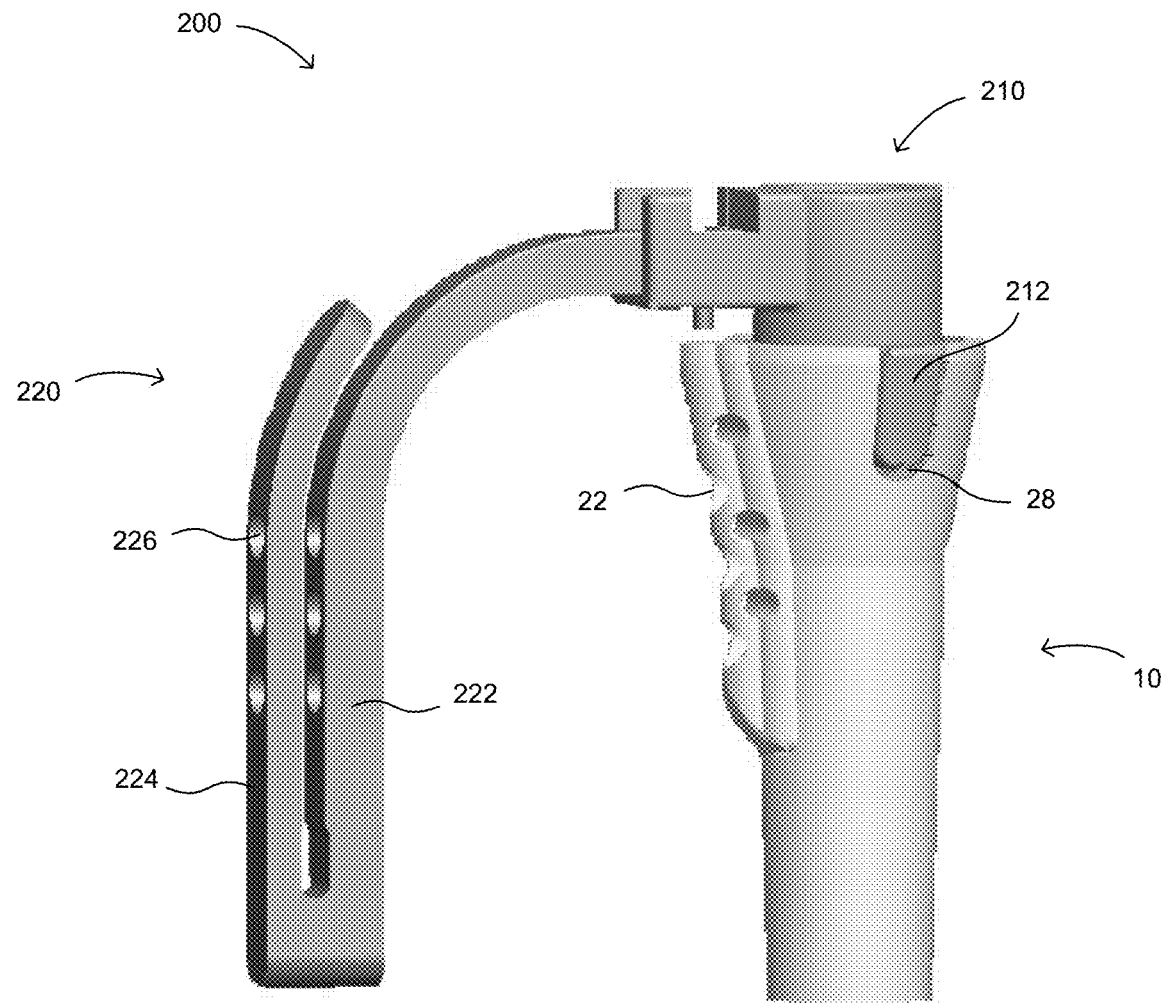
FIG. 4 is a perspective view of the void filling prosthesis of FIG. 1 and an aiming device.

FIG. 4 depicts an aiming device 200 that can be used when securing a threaded fastener to void filler 10 through bone and/or tissue. Once void filler 10 is implanted, bone and tissue may obscure the operator's view of fixation apertures 22 and 24. Aiming device 200 allows the operator to locate threaded openings 22 through such bone and tissue. Aiming device 200 generally includes a body 210 and aiming arm 220.

Body 210 may be cylindrical or frustoconical such that it fits within the channel of the metaphyseal portion. Alignment tabs 212 extend radially outwardly from body 210 so that they can engage with or slide within notches 28 within void filler 10. This engagement aligns aiming arm 220 with fixation prominence 16.

Aiming arm 220 can be connected to body 210 or in some embodiments may be integral with body 210, and generally includes a first guide portion 222 and a second guide portion 224. First guide 222 portion extends from body 210 and curves or turns in a distal direction. In one embodiment, first guide portion 222 may include an offset segment (not shown) that would be located adjacent to the aiming arm's connection to body 210. The offset segment may be offset laterally or medially to provide a clearance space for the patella and patella tendon during fixation.

First guide portion 222 also includes a plurality of guide apertures 226 that are aligned with threaded openings 22 when aiming device 200 is engaged with void filler 10. The second guide portion 224 is offset anteriorly from first guide portion 222 and also includes a plurality of guide apertures 226 that are also aligned with threaded openings 22 of void filler 10. This offset relationship helps stabilize a driving device when driving a threaded fastener into threaded opening 22.

In a wire fixation embodiment (not shown), an aiming arm may extend from body 210 in a lateral or medial direction when engaged to void filler 10 and align with passageways 24. In this embodiment, the wires may be passed through guide apertures in the aiming arm and punched or passed through the bone and through passageways 24.

In one embodiment of a method of use, void filler 10 may be utilized to reattach a bone fragment resected during a tibial tubercle osteotomy. Such attachment may be achieved by wire fixation, suture fixation, screw fixation, or the like. In a tibial tubercle osteotomy, a bone fragment underlying the tibial tubercle and patella tendon is at least partially resected so that the extensor mechanism can be moved aside to expose the primary or previously implanted prosthesis.

The prosthesis is removed from the tibia, and the bone is assessed for defects. An appropriate void filler is selected based on the size and shape of the defect, and a single reamer or a series of reamers are used to prepare the void for void filler 10. After a generally frustoconical void is formed in the metaphysis with a frustoconical reamer (not shown) that corresponds with head 136 and metaphyseal portion 12, head 136 of trial 130 may be placed into the void. If the proper depth of the head, as indicated by indicia 138, cannot be reached, the bone is successively reamed until the proper depth is achieved.

Thereafter, with head 136 securely placed within the void such that groove 139 generally faces anteriorly, reamer guide 120 is slid over shaft 132 of trial 130 until retaining sleeve 124 abuts abutment surface 134. Cutting head 112 is passed through slot 127 while bushing 140 is in a proximal position about cutting head 112 such that bushing 140 is proximal of guide collar 126 as cutting head 112 is passed through slot 127. Once cutting head 112 is within the retaining channel of guide collar 126, bushing 140 is advanced distally until it is fully seated within guide collar 126. Reamer 110 is then advanced into the bone to form a resected geometry to receive fixation prominence 16.

Depending on the condition of the bone and/or the extent of the bone defect, the tibial tubercle osteotomy may remove so much anterior bone that a slot in the anterior bone extending into the bone canal is exposed. Where this occurs, anterior reaming for fixation prominence 16 may not be warranted since there may be no anterior bone to resect. If this is the case, a rongeur may be used to shape the resected bone fragment to matingly engage fixation prominence 16 when reaffixing the fragment to the tibia.

Once the void has been sufficiently shaped, void filler 10 is inserted into the bone to achieve a press-fit relationship with the bone via impaction or some other means. This impaction or other means may occur until the proximal end of void filler 10 is either flush with or below the proximal end of the tibia.

Aiming device 200 is then attached to void filler 10 by inserting body 210 into metaphyseal portion 12 and by inserting the alignment tabs 212 into the notches 28 of metaphyseal portion 12. At this point aiming arm 220 is oriented in an anterior position external to the bone and aligned with fixation prominence 16. The fragment of bone that was removed by the tibial tubercle osteotomy is placed into a mating position against the tibia and a threaded fastener is advanced through guide apertures 226 of aiming device 200, through the bone, and into threaded openings 22 of void filler 10, thereby affixing the bone fragment to the tibia and void filler 10.

Once the bone fragment and patella tendon are secured, the tibial prosthesis, which preferably includes a baseplate and a stem, is affixed to the tibia. This may be performed by placing cement or some other adhesive into the channel of void filler 10 and or around the stem, and then inserting the stem into and through the channel such that at least a portion of the stem extends from the distal end of void filler 10.

As an alternative to a threaded fastener, cerclage wires may be utilized to fix the bone fragment to the tibia. In this embodiment method of fixation, an aiming device specific to wire or suture fixation is engaged to the implanted void filler 10. Wires are advanced through the guide apertures, through the bone, through passageways 24, and back out through the bone. The free ends of the wires extending from the bone are then used to affix the bone fragment to the tibia in the usual way.

In another method of wire fixation utilizing void filler 10, void filler 10 can be inserted such that fixation prominence 16 faces posteriorly. In this embodiment, wires can be passed through the bone and passageways 24 at a posterior region of the tibia and then wrapped around the tibia to secure the bone fragment. Alternatively, the wires may be wrapped around void filler 10 prior to implantation. This may be achieved by selecting a void filler 10 that is sized to be cemented into the bone, rather than press-fit, or a void filler 10 with channels to house the wires as void filler 10 is impacted into the bone.

Turning to another method embodiment, void filler 10 may be utilized to make other repairs such as the repair of a ruptured patella tendon. In this embodiment void filler 10 is utilized in a similar fashion as with a tibial tubercle osteotomy. For example, where the patella tendon is ruptured, a bone plug and tendon allograft may be harvested and implanted into the tibia. In this embodiment, void filler 10 is implanted into the bone, aiming device 200 engaged to void filler 10, and the bone plug either fixed to void filler 10 and bone via threaded fastener or via wire fixation, as previously described.

Still other types of procedures are possible utilizing void filler 10 described herein. For example, void filler 10 may be used in procedures involving uncontained defects or other bone defects or repairs that require the use of morselized bone graft and metal mesh to contain the bone graft material. In such a procedure, void filler 10 and fixation apertures extending therein may be used to help fix the mesh to void filler 10. In this scenario, fixation prominence 16 may be a plurality of bumps each containing threaded opening 22 or passageway 24 wherein the bumps and fixation apertures may be utilized to help secure the wire mesh to the bone to facilitate a solid containment unit for the morselized bone graft, particularly as the graft material is being impacted into the bone.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of replacing a joint at an end of a bone, comprising:
   inserting a void filling prosthesis into a void at the end of the bone, the void filling prosthesis having an outer surface, at least one opening extending into the outer surface, and a channel extending entirely through the void filling prosthesis along its length from a joint-facing end to an interior-facing end, the channel being configured to receive a stem of a joint prosthesis;
   driving a fastener through the bone from an outer surface thereof into the opening of the void filling prosthesis to secure the void filling prosthesis to the bone; and
   implanting the joint prosthesis onto the end of the bone by initially advancing the joint prosthesis through the joint-facing end of the void filling prosthesis and into the channel.

2. The method of claim 1, wherein the fastener is a threaded fastener, the opening in the outer surface of the void filling prosthesis is a threaded opening, and the driving step includes engaging the threaded opening with the threaded fastener.

3. The method of claim 2, further comprising connecting an aiming device to an end of the void filling prosthesis, the aiming device having a guide aperture aligned with the threaded opening when the aiming device is connected to the void filling prosthesis.

4. The method of claim 3, wherein the driving step includes advancing the threaded fastener through the guide aperture of the aiming device.

5. The method of claim 1, wherein the implanting step includes inserting the stem of the joint prosthesis into and through the channel such that at least a portion of the stem extends from the interior-facing end of the void filling prosthesis.

6. The method of claim 5, further comprising placing cement within the channel of the void filling prosthesis.

7. The method of claim 1, wherein the bone includes a first portion and a second portion separated from the first portion, and the driving step includes driving the fastener through the second portion to secure the second portion to the first portion.

8. The method of claim 1, wherein the bone is one of a tibia, femur, and humerus.

9. The method of claim 1, further comprising forming the void using a reamer received in a guide collar of a guide member, the guide member being attached to a shaft of a trial received in a portion of the void formed prior to use of the reamer, wherein an operational axis of the guide collar is at an oblique angle relative to an insertion axis of the trial.

10. The method of claim 1, wherein at least a portion of the outer surface of the void filling prosthesis includes a porous structure.

11. A method of replacing a joint at an end of a bone, comprising:
    removing a previously implanted joint prosthesis from an end of a bone;
    inserting a void filling prosthesis into a void at an end of the bone, the void filling prosthesis having an outer surface and at least one opening in the outer surface;
    advancing a fastener through the bone from an outer surface thereof into the opening of the void filling prosthesis to secure the void filling prosthesis to the bone; and
    implanting a new joint prosthesis onto the end of the bone such that after a leading end of the new joint prosthesis is advanced beyond the end of the bone and into the void filling prosthesis, the leading end advances in a direction away from the end of the bone.

12. The method of claim 11, wherein the fastener is a wire, and the opening of the void filling prosthesis is a through-opening.

13. The method of claim 11, wherein the fastener is a threaded fastener, and the opening is a threaded opening.

14. The method of claim 13, further comprising connecting an aiming device to the void filling prosthesis, and the advancing step includes advancing the threaded fastener through the aiming device.

15. The method of claim 11, further comprising forming the void with a reamer by cutting the bone along an axis at an angle relative to a central longitudinal axis of the joint prosthesis.

16. The method of claim 11, wherein the bone is a tibia.

17. The method of claim 11, wherein the bone is a femur, and the end of the femur is a distal end of the femur.

18. The method of claim 11, wherein the implanting step includes passing a stem of the new joint prosthesis through a channel in the void filling prosthesis.

19. The method of claim 18, wherein the opening in the outer surface of the void filling prosthesis extends in a direction transverse to an axis defined by the channel.

20. The method of claim 15, further comprising positioning a frustoconical head of a trial into a preliminary void at the end of the bone prior to inserting the reamer through a guide collar attached to the trial, the preliminary void being smaller than the void.

\* \* \* \* \*